United States Patent [19]
Wright

[11] Patent Number: 5,241,100
[45] Date of Patent: Aug. 31, 1993

[54] MONOCARBOXYLIC ACID ESTERS AND OLEFIN POLYMER COMPOSITION STABILIZED THEREWITH

[75] Inventor: Charles M. Wright, Wilmington, Del.

[73] Assignee: Himont Incorporated, Wilmington, Del.

[21] Appl. No.: 730,330

[22] Filed: Jul. 15, 1991

Related U.S. Application Data

[63] Continuation-in-part of Ser. No. 579,906, Sep. 10, 1990, abandoned.

[51] Int. Cl.$^5$ .............................................. C07C 69/74
[52] U.S. Cl. .......................................... 560/7; 560/100
[58] Field of Search ...................................... 560/100, 7

[56] References Cited

U.S. PATENT DOCUMENTS

| | | | |
|---|---|---|---|
| 2,201,237 | 5/1940 | Littmann | 560/7 |
| 2,207,890 | 7/1940 | Littmann | 560/7 |
| 2,319,696 | 5/1943 | Littmann | 560/7 |
| 2,703,796 | 3/1955 | Ritchie | 560/7 |
| 2,750,373 | 6/1956 | Bible | 560/7 |
| 2,750,405 | 6/1956 | Ritchie | 560/7 |
| 3,998,863 | 12/1976 | Song et al. | 554/228 |

*Primary Examiner*—Paul J. Killos

[57] ABSTRACT

Disclosed are 2,4,6-trialkyl-3-hydroxybenzyl esters of monocarboxylic resin acids and olefin polymer compositions stabilized therewith.

3 Claims, No Drawings

MONOCARBOXYLIC ACID ESTERS AND OLEFIN POLYMER COMPOSITION STABILIZED THEREWITH

This application is a continuation-in-part of the U.S. patent application Ser. No. 07/579,906, filed Sep. 10, 1990, now abandoned.

FIELD OF THE INVENTION

This invention relates to the chemical arts. More particularly, this invention relates to novel compounds useful as stabilizers in olefin polymer compositions and to the olefin polymer compositions stabilized therewith.

BACKGROUND OF THE INVENTION

Olefin polymers formed by the polymerization of olefin monomers in the presence of a Ziegler-Natta catalyst have a high degree of crystallinity and beneficial physical properties which make them particularly useful in the production of molded articles, films and fibers. Ziegler-Natta catalysts are formed by the reaction of an inorganic compound of a metal of Groups I-III of the Periodic Table, such as an aluminum trialkyl, with a compound of a transition metal of Groups IV-VIII of the Periodic Table, such as titanium tetrahalide. Olefin polymers which are both stereoregular and sterospecific are formed by the polymerization of olefin monomers in the presence of certain Ziegler-Natta type catalysts. Typically the crystallinity is from about 20 to about 90% as determined by X-ray diffraction.

Notwithstanding the very desirable and beneficial properties of these olefin polymers, they are quite susceptible to oxidative degradation due to exposure to atmospheric agents over time and to exposure to thermal procedures, particularly at the elevated temperatures used over the period of time required to process, e.g., mill, mold, extrude, and spin, the olefin polymers. Hence, a number of stabilizers have been developed over the years which tend to inhibit the oxidative degradation of these olefin polymers. However, these stabilizers suffer from one or more deficiencies. For example, they have an adverse affect on the physical properties of the olefin polymers during processing, they fail to provide a product which has any appreciable storage stability, they bloom or they provide a product which is prone to gas yellowing.

Gas yellowing occurs during the production of fibers or films from olefin polymers which have been stabilized with phenolic stabilizers or during the storage of olefin polymers, especially when stored in particulate form, such as, powder or flake. It has been shown that such gas yellowing is typically caused by nitration or nitrosation of certain hindered phenolic stabilizers in the para position with the oxides of nitrogen present in the atmosphere.

To prevent nitration or nitrosation in the para position, phenolic stabilizers having an ester group in the meta position, such as those disclosed in U.S. Pat. Nos. 3,795,700, 3,998,863 and 3,923,869, were developed. These ester groups tend to sterically or otherwise hinder nitration or nitrosation at the para position. However, these stabilizers either have minimal compatibility with olefin polymers or have minimal solubility with the solvents used in "in-process" stabilization or both.

A costabilizer system for polyolefins containing 1) a hindered phenol and 2) an ester formed by reacting a sulfur-containing aliphatic carboxylic acid with certain cyclic terpene alcohols or hydrogenated derivatives thereof, such as tetrahydroabietyl alcohol, is disclosed in U.S. Pat. No. 3,630,991.

U.S. Pat. Nos. 4,775,496 and 4,946,879 describe antidegradants for rubber compounds consisting of the reaction product of a rosin acid and a polyfunctional compound having at least one functional group capable of reaction with a carboxylic acid functionality and another functional group having antidegradant properties selected from the group consisting of 4-hydroxymethyl-2,6-di-t-butylphenol, 4,4'-methylenebis-(2,6-di-t-butylphenol), 4,4'-butylidenebis-(6-t-butyl-3-methylphenol), 4,4'-thiobis-(6-t-butyl-m-cresol), 4,4'thiobis-(6-t-butyl-o-cresol), 2-mercaptobenzimidazole, p-aminodiphenylamine, p-hydroxy-diphenylamine, p-hydroxy-p'-amine-diphenylamine and p,p'-diamino-diphenylamine.

SUMMARY OF THE INVENTION

This invention provides a new class of stabilizers for olefin polymers which inhibit the oxidation, including the gas yellowing and discoloration of olefin polymers, and which are compatible with olefin polymers and miscible with solvents typically used in "in-process" stabilization. These new stabilizers are esters of monocarboxylic acids commonly referred to as resin acids. The esters have the general formula:

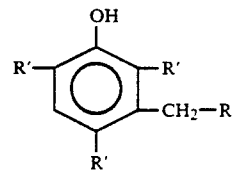

wherein R is a saturated or unsaturated carboxyl radical having 20 carbon atoms (including the carbon of the carboxyl) and R' is the same or different $C_{1-8}$ normal or branched alkyl radical.

This invention further relates to olefin polymer compositions stabilized with an effective amount of the esters having the above general formula.

DETAILED DESCRIPTION OF THE INVENTION

All percentages are by weight unless otherwise indicated. Ambient or room temperature is approximately 25° C.

In the above general formula, typical R radicals include abietyl, neoabietyl, tetrahydroabietyl, dehydroabietyl, dihydroabietyl, pimaryl, levopimaryl, dextropimaryl, isodextropimaryl, tetrahydropimaryl and dihydropimaryl; and suitable R' alkyl groups include methyl, ethyl, propyl, isopropyl, tertiarybutyl, 2-methylbutyl, 3-methylbutyl, 2-ethylbutyl, 3-ethylbutyl, 2-methyl-3-ethylbutyl, 2-methylpentyl, 3-methylpentyl, 2-ethylpentyl, 3-ethylpentyl, 2-methyl-3-ethylpentyl, 2-methylhexyl, 3-methylhexyl, 4-methylhexyl, 2-ethylhexyl, 3-ethylhexyl, 4-ethylhexyl, 2-methylheptyl, 3-methylheptyl, 4-methyl-heptyl, and 5-methylheptyl.

Preferably, the esters of this invention are prepared by reacting a resin acid material or mixtures thereof with a benzyl chloride in a suitable solvent. An alternative method is the transesterification of the ester of the resin acid with a benzyl alcohol, in the absence or presence of a solvent.

Resin acids are found in wood rosin, gum rosin and tall oil rosin. Resin acids are typically classified either as an abietic type or a pimaric type according to the distinguishing features set forth in Encyclopedia of Chemical Technology, Vol. II, 779, 786-87 (1953). Hence, resin acids useful in the practice of this invention include abietic acid, neoabietic acid, dehydroabietic acid, dihydroabietic acid, tetrahydroabietic acid, palustric acid pimaric acid, levopimaric acid, dextropimaric acid, isopimaric acid, dihydropimaric acid and tetrahydropimaric acid. Mixtures of these acids can be used.

The individual resin acids may be used as isolated entities. Techniques for isolating resin acids are described in the aforementioned Encyclopedia of Chemical Technology reference, page 484.

Hydrogenated resin acid materials and mixtures thereof can also be used and are preferred. As used herein, the term "hydrogenated resin acid material" means any resin acid material in which the ethylenic unsaturation of the resin acids thereof are partially or substantially completely hydrogenated. Typically a partially hydrogenated resin acid material is hydrogenated to the extent that 40 to 60% of its total ethylenic unsaturation has been saturated. A substantially completely hydrogenated resin acid material usually has greater than 60% up to about 98%, preferably about 65% to about 95%, most preferably about 65% to 90% of its total ethylenic unsaturation saturated with hydrogen. Substantially completely hydrogenated resin acid materials are generally referred to by the manufacturers of same as highly hydrogenated rosin or resin materials. Preferred resin acid materials are the substantially completely hydrogenated resin acid materials which are available commercially. Typically the resin acids useful in the practice of this invention have a bromine no. from 5 to 28.

Hence, the resin acid material may be a resin acid or a hydrogenated derivative thereof, or any combination or mixture of such resin acid materials.

Typical benzyl chlorides include 2,6-dimethyl-3-hydroxy-4-tert-butylbenzyl chloride, 4,6-dimethyl-3-hydroxy-2-tert-butylbenzyl chloride, 2,4-dimethyl-3-hydroxy-6-tert-butylbenzyl chloride, 2,4-di-tert-butyl-3-hydroxy-6-methylbenzyl chloride, 4,6-di-tert-butyl-3-hydroxy-2-methylbenzyl chloride, 2,6-di-tert-butyl-3-hydroxy-4-methylbenzyl chloride, and 2,4,6-tri-tert-butyl-3-hydroxybenzyl chloride. The preferred benzyl chloride is 2,6-dimethyl-3-hydroxyl-4-alkylbenzyl chloride where the alkyl has 3 to 18 carbon atoms. Benzyl chloride are commercially available or can be prepared by known methods, such as the light-induced chlorination of alkyl benzenes with molecular chlorine and the chlorination of alkyl benzenes with t-butyl hypochlorite initiated by azobis-isobutyronitrile.

Suitable solvents for the preparation of the esters include triethylamine, methylene chloride and toluene. Triethylamine is the preferred solvent.

Olefin polymers which can be stabilized by the esters of this invention are those prepared by the polymerization of $C_{2-10}$ olefin monomers or the copolymerization terpolymerization of one such olefin monomer with a different or two different, as the case may be, such olefin monomers, which polymers have a crystallinity or semi-crystallinity, as determined by X-ray diffraction, of from 20 to about 90%.

The preferred olefin polymer is a propylene polymer material. Suitable propylene polymer materials include (a) a homopolymer of propylene; (b) a random copolymer of propylene and an olefin selected from the group consisting of ethylene, and $C_4$-$C_{10}$ 1-olefins, provided that, when the olefin is ethylene, the maximum polymerized ethylene content is about 10 (preferably about 4) percent by weight, and, when the olefin is a $C_4$-$C_{10}$ 1-olefin, the maximum polymerized content thereof is about 20 (preferably about 16) percent by weight; (c) a random terpolymer of propylene and an olefin selected from the group consisting of ethylene and $C_4$-$C_8$ 1-olefins, provided that the maximum polymerized $C_4$-$C_8$ 1-olefin content is about 20 (preferably about 16) percent by weight, and, when ethylene is one of the olefins, the maximum polymerized ethylene content is about 5 (preferably about 4) percent by weight; or (d) a homopolymer of (a) or random copolymer of (b) which is impact-modified with an ethylene-propylene rubber in a reactor or series of reactors in the presence of (a) or (b) as well as by physical blending (a) or (b) with the rubber until a homogeneous blend is obtained. The ethylene-propylene rubber content of (d) being from about 5 to about 40% and the ethylene content of said rubber being from about 7 to about 60%, preferably from about 10 to about 40%.

The $C_4$-$C_{10}$ 1-olefins include the linear and branched $C_4$-$C_{10}$ 1-olefins such as, for example, 1-butene, 1-pentene, 3-methyl-1-butene, 4-methyl-1-pentene, 1hexene, 3,4-dimethyl-1-butene, 1-heptene, 3-methyl-1-hexene, and the like.

Propylene homopolymers and random copolymers of propylene are most preferred.

In general 0.005 to 3%, by weight of the olefin polymer, of the ester stabilizer of this invention can be used to stabilize olefin polymers and compositions based on olefin polymers. Typically, 0.01 to 0.5 is used, preferably 0.01 to 0.3 is used, most preferably 0.01 to 0.15 to 0.25.

The stabilizers of this invention do not need a costabilizer. However, heat stabilizers, such as distearyl thiodipropionate (DSTDP) or dilauryl thiodipropionate (DLTDP), light stabilizers, such as bis(2,2,6,6-tetramethyl piperidyl)sebacate, and polymeric light stabilizers such as N,N'-bis(2,2,6,6-tetramethyl-4-piperidinyl)-1,6-hexanediamine, polymer with 2,5,6-trichloro-1,3,5-triazine and 2,4,4-trimethyl-1,2-pentanamine or melt stabilizers such as tris(2,4-di-tert-butylphenyl)phosphite, a stabilizer composition the main component of which is tetrakis-(2,4-di-tert-butylphenyl)-4,4'-biphenylene diphosphonite and tris(4-nonylphenyl)phosphite (TNPP), can be used in addition to the stabilizer of this invention. If such stabilizers are used, they typically are present in an amount from about 0.01% to 0.30% by weight of total composition.

In addition, the polyolefins may contain other conventional additives such as antacids, peroxides, pigments and fillers.

The following examples illustrate the specific embodiments of the instant invention.

In the examples, the benzyl chloride as received from the manufacturer contained 83% benzyl chloride. The benzyl chloride was distilled to remove any unidentified heavy impurities and the methylisobutyl ketone (MIBK) solvent in two glass-lined LUVA-type thin film distillation apparatus, operating continuously, provided with a vacuum system. The first and second condensers were water-cooled at 15° C. with each collection vessel therefor being cooled to −50° C. to recover most of the MIBK in the first step and to recover the crystallized benzyl chloride in the second step. The collection vessel was changed under vacuum in between the first and second steps.

EXAMPLE 1

This example illustrates an ester of this invention and a process for making same.

Into a reaction vessel equipped with a mechanical stirrer, condenser and nitrogen sparge are added 0.2 moles 2,6-dimethyl-3-hydroxy-4-t-butylbenzyl chloride and 0.24 moles Foral HH tetrahydroabietic acid having a bromine number of 8 (a highly hydrogenated resin material from Hercules Incorporated) and 200 ml triethylamine. The ingredients are refluxed for 18 hours at 88° to 92° C. under a nitrogen atmosphere. The reaction mixture is allowed to stand until it has cooled to room temperature. 200 mls of dichloromethane is added to the reaction mixture and the mixture is filtered to remove the precipitated triethanol-amine-hydrochloride salt. The supernatant liquid is purified by washing with multiple (2 to 4) aliquots of 1% aqueous solution of hydrochloric acid. The organic layer is separated and dried over anhydrous magnesium chloride at room temperature. The solvent is then removed by vacuum distillation and 36 g of a white crystalline powder is recovered having a melting Point of 159.4° C. Proton, carbon$^{13}$ NMR and IR analysis confirmed the ester structure of the resultant powder to be an 2,6-dimethyl-3-hydroxy-4-t-butylbenzyl tetrahydroabietate. The melting point of the ester is 159° C.

EXAMPLE 2

The procedure and ingredients of Example 1 are used except that Foral DX abietic acids (a mixture of tetrahydro, dihydro and dehydro abietic acids from Hercules Incorporated) having a bromine number of 13 is used instead of Foral HH tetrahydroabietic acid. 30 g of an off white amorphous product is recovered. Proton, carbon$^{13}$ NMR and IR analysis confirmed the oil to be a mixture of 2,6-dimethyl-3-hydroxy-4-t-butylbenzyl tetrahydroabietates and isomers.

EXAMPLE 3

The procedure and ingredients of Example 1 are used except that Foral AX abietic acids (a mixture of tetrahydro, dihydro and dehydro abietic acids from Hercules Incorporated) having a bromine number of 26 is used instead of Foral HH tetrahydroabietic acid. 30 g of a slightly yellow viscous oil is recovered. Proton, carbon$^{13}$ NMR and IR analysis confirmed the oil to be a mixture of 2,6-dimethyl-3-hydroxy-4-t-butylbenzyl tetrahydroabietates and isomers.

The effect of unsaturation in the resin acid used to prepare the ester is shown in Table I below.

TABLE I

| Example No. | Bromine Number | Unsaturation % | Product Color | Yield | Morphology |
|---|---|---|---|---|---|
| 1 | 5 | 2 | white | 78 | solid |
| 2 | 13 | 10 | pale | 60 | amorphous |
| 3 | 26 | 22 | yellow | 60 | viscous |

EXAMPLE 4

This example illustrates the use of an ester of this invention in the stabilization of a propylene polymer.

The ester of Example 1 and the conventional stabilizers set forth in Table II are melt compounded with 100 parts of polypropylene and 0.1 part calcium stearate in the amounts as set forth in Table II until a homogeneous mixture is formed. Part of the mixture is then injection molded into 50 mil×$\frac{1}{2}$"×5" plaques using an ASTM #3 mold. The long term oven aging is conducted on these plaques according to HIMONT Test Method PTC 104, available from HIMONT Incorporated. Another part of the mixture is injection molded into 40 mil×3"×3" plaques using a Hoescht mold and the color is measured on these plaques according to the procedures of ASTM D1925-70 Section I using a Hunter D25P-2 colorimeter in the total transmission mode (which had been standardized using air as a reference) using three injection molded plaques 40 mil (0.042") thick from each sample. Yellowness is defined as the deviation in chroma from whiteness in the dominant wavelength range from 570 to 580 nm. The Yellowness Index is a measure of the magnitude of yellowness relative to magnesium oxide standard reference. The lower the number the better the color.

Stocks 1, 2 and 6 are illustrative of this invention. Stocks 3, 4, 5 and 7 are comparatives.

TABLE II

| Ingredients | Stocks | | | | | | |
|---|---|---|---|---|---|---|---|
| | 1 | 2 | 3 | 4 | 5 | 6 | 7 |
| Polypropylene[1] | 100 | 100 | 100 | 100 | 100 | 100 | 100 |
| Calcium Stearate | 0.1 | 0.1 | 0.1 | 0.1 | 0.1 | 0.1 | 0.1 |
| 2,6-dimethyl-3-hydroxyl-4-t-butyl benzyl tetra-hydroabietate | 0.1 | 0.3 | — | — | — | 0.1 | — |
| Cyanox 1790 stabilizer | — | — | 0.1 | 0.3 | — | — | 0.1 |
| Irganox 1076 stabilizer | — | — | — | — | 0.1 | — | — |
| Distearyldithio-propionate | — | — | — | — | — | 0.1 | 0.1 |
| Properties: | | | | | | | |
| Air aging at 150° C., days to embrittlement | 5 | 7 | 8 | 7 | 7 | 22 | 34 |
| Yellowness Index | 2.0 | 0.7 | 7.7 | 16.9 | 1.7 | −0.5 | 2.4 |

[1]Pro-fax 6501 crystalline homopolymer of propylene in flake form having an intrinsic viscosity of 2.5 and a melt flow of 3–5 dg/min. and being free of all additives.

The results show that polypropylene stabilized with the esters of this invention maintain comparable aging performance and have excellent color as compared to polypropylene stabilized with equivalent concentrations of conventional stabilizers.

EXAMPLE 5

This example illustrates the gas yellowing susceptibility of the ester of this invention.

A solution of 0.1 parts the ester of Example 1 in 30% diethyl ether is applied to 100 part of a propylene homopolymer in flake form free of all additives. The thus treated polymer flake was dried under a nitrogen sparge and then extruded into fibers with a spin finish that does not exhibit 2×4 inches and the swatches tested for gas yellowing according to the procedures of AATCC Procedure 23-1983 modified by using nitrous oxide and methane in the fume chamber to accelerate the test procedure.

The formulation and procedure as set forth above was used except that Irganoz 1076 and Cyanox 1790 stabilizers, respectively, were used in place of the ester of Example 1.

The results of the test are set forth in Table III. Stock 1 is illustrative of this invention and Stocks 2 and 3 are comparative illustrations. The rating scale is from 1 to 5 with 1 being the lowest rating and indicating failure and 5 being the highest rating and indicating negligible or no discoloration.

TABLE III

| Ingredients | Stocks | | |
|---|---|---|---|
| | 1 | 2 | 3 |
| Polypropylene[1] | 100 | 100 | 100 |
| 2,6-dimethyl-3-hydroxyl-4-t-butyl benzyl tetrahydroabietate | 0.1 | — | — |
| Cyanox 1790 stabilizer | — | 0.1 | — |
| Irganox 1076 stabilizer | — | — | 0.1 |
| Gas Yellowing Properties: | | | |
| 15 minute | 5 | 5 | 5 |
| 2 cycles | 4–5 | 4–5 | 3–4 |

[1]Pro-fax 6501 crystalline homopolymer of propylene in flake form having an intrinsic viscosity of 2.5 and a melt flow of 3–5 dg/min. and being free of all additives.

The results shown in Table III show that the ester of this invention does not contribute to significant gas yellowing after two cycles of exposure.

EXAMPLE 5

This example illustrates the oxidative stability on storage of polyproylene stabilized with the ester of this invention.

The procedure of Example 4 using 100 parts of the polypropylene of Example 4 and 0.1 part calcium stearate was used with the ester of Example 1 and conventional stabilizers in the amount set forth in Table IV below.

TABLE IV

| Stabilizer | Concentration. ppm | Days to Failure[1] |
|---|---|---|
| 2,6-dimethyl-3-hydroxyl-4-t-butyl benzyl tetrahydroabietate | 50 | 7 |
| 2,6-dimethyl-3-hydroxy-4-t-butyl benzyl tetrahydroabietate | 150 | 15 |
| Cyanox 1790 stabilizer | 50 | 7 |
| Cyanox 1790 stabilizer | 150 | 10 |
| Irganox 1076 stabilizer | 50 | 10 |
| Irganox 1076 stabilizer | 150 | 65 |

[1]The length of time at 90° C. to achieve a 5% decrease in the intrinsic viscosity. The initial intrinsic viscosity in all cases was about 2.0 dg/10 min.

The above table shows that the oxidative storage stability of the ester of our invention is comparable to the oxidative storage stability of conventional stabilizers at a concentration of 50 ppm, is better than Cyanox 1790 stabilizer but not as good as Irganox 1076 stabilizer at a concentration of 150 ppm. However, as shown in Table III, Irganox 1076 stabilizer is susceptible to gas yellowing.

EXAMPLE 6

This example illustrates the solubility of an ester of this invention in a propylene polymer.

The ester of example 1 and the conventional stabilizer set forth in Table V are melt compounded with 35 g of Pro-fax 6300 crystalline homopolymer of propylene having a melt flow rate of 10 and a density of 0.903 g/cm$^3$ and free of all additives in a Brabende torque rheometer at 180° C. for 7 minutes and 60 rpm until a homogeneous mixture is formed. The mixture is initially cold pressed and then compression molded using a 100 ton Daniel press with electrically heated platens to prepare 5 cm×5 cm×3 mm, additive-containing plaques. The mixture is pressed initially at 180° C. for 2 minutes at zero pressure followed by one minute pressing under full pressure. Then the plaques are cooled to room temperature, approximately for 15 minutes, under full pressure.

The same procedure was used to prepare 5 cm×5 cm×250 μm additive-free polypropylene films except that 160° C. was used during a one minute preheat time followed by one minute under full pressure.

The solubility was measured using a solubility cell having four stacks as described in Al-Malaika et al., Polymer Degradation and Stability, 32, 231–247, (1991), each stack having three of the additive-free polypropylene films described above, which were heated for 1 hour at 120° C. under nitrogen, sandwiched between two of the additive-containing plaques described alone, which were supersaturated with the particular additive at 60° C. The four stacks were placed in the solubility cell between a top and bottom metal casing. Pressure was applied symmetrically by compression springs to remove air bubbles and achieve intimate contact between the layers of the films and the plaques. The solubility cell was then placed in a vacuum oven at 60° C. (±2° C.). The established equilibrium is monitored at intervals. Once the additive concentration in the film layers of a stack reached a constant value the experiment was terminated. The concentration of the diffusant in the additive-free polymer film of the stack was determined by using a Beckman DU-7 high speed UV/VIS spectrophotometer and a Perkins-Elmer 599 infrared spectrophotometer.

TABLE V

| Stabilizer | Solubility (wt %) @ 60° C. (±2° C.) | |
|---|---|---|
| | UV Abs. | IR Abs. |
| 2,6-dimethyl-3-hydroxy-4-t-butyl-benzyl tetrahydroabietate | 0.154 | 0.160 |
| Cyanox 1790 stabilizer | 0.063 | 0.061 |

As demonstrated above in Table V, the solubility of the ester of the present invention is much higher than the solubility of the conventional stabilizer. Thus, evidencing better compatibility of the esters of the present invention.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. An ester having the formula:

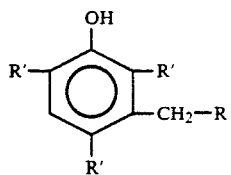

wherein R is a saturated or unsaturated carboxyl radical having 20 carbon atoms selected from the group consisting of abietyl, neoabietyl, tetrahydroabietyl, dehydroabietyl, dihydroabietyl, pimaryl, levopimaryl, dextropimaryl, isodextropimaryl, tetrahydropimaryl and dihydropimaryl and R' is the same or different $C_{1-8}$ normal or branched alkyl radical.

2. The ester of claim 1 wherein R is tetrahydroabietyl.

3. The ester of claim 1 wherein R is tetrahydroabietyl, R' ortho the hydroxy group is methyl, the other R' ortho the hydroxy group is t-butyl and R' para the hyroxyl group is methyl.

* * * * *

UNITED STATES PATENT AND TRADEMARK OFFICE
CERTIFICATE OF CORRECTION

PATENT NO.  :  5,241,100

DATED       :  August 31, 1993

INVENTOR(S) :  Charles M. Wright

It is certified that error appears in the above-identified patent and that said Letters Patent is hereby corrected as shown below:

At col. 6, line 58, after "exhibit" insert --gas yellowing. The fibers were then woven into swatches--.

At col. 8, line 2, change "Brabende" to --Brabender--.

Signed and Sealed this

Twenty-second Day of March, 1994

Attest:

BRUCE LEHMAN

*Attesting Officer*　　　　*Commissioner of Patents and Trademarks*